Figure 1:
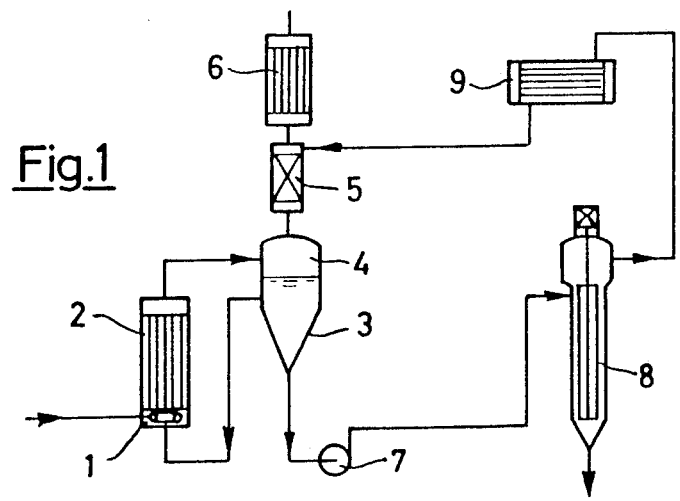

United States Patent [19]

Fuchs et al.

[11] 3,954,751
[45] May 4, 1976

[54] CONTINUOUS PRODUCTION OF CYANURIC ACID

[75] Inventors: Hartwig Fuchs, Ludwigshafen; Reinhard Billet, Mannheim; Horst Goelz, Schwetzingen; Hubert Suter, Ludwigshafen; Karl Von Erden, Altrip, all of Germany

[73] Assignee: BASF Aktiengesellschaft, Ludwigshafen, Germany

[22] Filed: Dec. 28, 1973

[21] Appl. No.: 429,089

[30] Fogeign Application Priority Data
Jan. 2, 1973   Germany.................... 2300037

[52] U.S. Cl............................................ 260/248 A
[51] Int. Cl.².................................... C07D 251/32
[58] Field of Search............................ 260/248 A

[56] References Cited
UNITED STATES PATENTS

| | | |
|---|---|---|
| 3,093,641 | 6/1963 | Formaini............................ 260/248 |
| 3,172,886 | 3/1965 | Christoffel et al................. 260/248 |
| 3,524,853 | 8/1970 | Saito et al......................... 260/248 |
| 3,758,572 | 9/1973 | Jones et al...................... 260/248 X |
| 3,761,474 | 9/1973 | Mesiah.............................. 260/248 |

*Primary Examiner*—John M. Ford
*Attorney, Agent, or Firm*—Johnston, Keil, Thompson & Shurtleff

[57] ABSTRACT

A process for the production of cyanuric acid in which urea and an inert solvent are passed into a reaction zone in which pyrolysis of the urea with the formation of cyanuric acid takes place at 200° to 300°C, from 50 to 760 mm and a space-time yield of from 0.1 to 2 kg of cyanuric acid per liter of reaction volume per hour, and the cyanuric acid is separated in a crystal separation zone and freed from solvent in a falling film evaporator.

3 Claims, 3 Drawing Figures

CONTINUOUS PRODUCTION OF CYANURIC ACID

The present invention relates to a novel and very advantageous process for the continuous production of cyanuric acid by pyrolysis of urea in an inert solvent which makes it possible to manufacture cyanuric acid of high purity in a high yield.

Several methods for the production of cyanuric acid are known in which urea is heated either directly or by means of a solvent which serves as a heat transferrer. In direct heating (for example German Laid-Open Specification No. 1,470,140) the solid urea passes through a liquid to pasty condition back into a solid state and for this fairly high pyrolysis temperatures, special reaction apparatus and addition of for example previously granulated cyanuric acid are necessary. The disadvantage that byproducts are formed which have to be converted into cyanuric acid in a second stage by repeated hydrolysis has to be tolerated in this method. Moreover continuous operation is made difficult by the fact that the proportion of urea which sublimes off with the ammonia and has to be returned to the reaction zone agglomerates with the reaction product in the apparatus.

When pyrolysis of urea is carried out in a liquid as heat transferrer the formation of byproducts is unavoidable so that it has to be followed by hydrolysis.

True solvents for urea have also already been proposed as heat transferrers. Thus for example according to the method described in German Laid-Open Specification No. 2,014,916 alkyl-sulfones are used. These solvents have proved however not to be inert enough under the conditions of the pyrolysis of urea, so that cleavage reactions with the formation of troublesome byproducts occur which prevent satisfactory continous operation. Another difficulty is that it is not possible to dispense with washing with more volatile solvents such as water or methanol to isolate the cyanuric acid separated from the liquid.

We have now found that cyanuric acid can be prepared in a continuous operation by pyrolysis of urea and/or biuret in the presence of an inert solvent while avoiding the said difficulties when a. molten urea or a solution of urea in a solvent is supplied to an externally heated tubular reactor or thin-layer reactor in which the urea is decomposed into cyanuric acid and ammonia in the presence of a solvent at a temperature of from 200° to 300°C at a pressure of from 50 to 760 mm in spacetime yield of from 0.1 to 2 kg and preferably from 0.5 to 1.5 kg of cyanuric acid per liter of reaction volume per hour;

b. the reaction mixture is passed to a crystal separation zone and at the same time the mixture of ammonia and vaporized solvent is fed into a condensation zone from which the condensed solvent is returned to the reaction zone;

c. the cyanuric acid which has crystallized out in the form of a mash from the reaction mixture in the crystal separation zone is transferred to a falling film evaporator, the liquid reaction mixture supplied in excess to the crystal separation zone is returned to the reaction zone; and d. the mash consisting of crystallized cyanuric acid and solvent is freed from solvent in the falling film evaporator at a temperature of from 100° to 250°C and a pressure of from 1 to 300 mm and the solvent is returned to the reaction zone after condensation.

An inert solvent in the context of the present invention is an organic solvent in which urea is soluble, which does not undergo any detectable change under the conditions of the pyrolysis, does not react chemically to any detectable extent and which boils in the range from 200° to 300°C without decomposition.

Examples of solvents of this type are N-cyclohexyl-pyrrolidone-(2) and N-cyclohexyl-4,4-dimethylpyrrolidone-(2).

The urea required for the process is supplied in molten condition or dissolved in a solvent, preferably at a temperature of from 130° to 140°C, conveniently through a dosing or distributing means 1 such as a nozzle or venturi tube, into a reaction zone 2 which is heated externally.

The reaction zone may be formed by a tubular or thin layer reactor whose tubes are surrounded by a heat-exchange medium. When adding molten urea or a solution of urea in the solvent, solvent is placed in the reactor when starting up. By supplying heat (in the case of the tubular reactor by means of the heat-exchange medium surrounding the tubes) pyrolysis of the urea with the formation of cyanuric acid and ammonia takes place during the flow of the reaction mixture through the tubes of the reactor at temperatures of 200° to 300°C and preferably of 220° to 250°C and pressures of from 50 to 760 mm and preferably of from 300 to 500 mm.

The large surface area between the liquid space and the gas space provided by the tubular reactor or falling film reactor makes it possible for the ammonia formed in the pyrolysis to leave the liquid phase rapidly. The supply of urea in relation to the amount of solvent is advantageously such that the liquid reaction mixture has a solids content of from 2 to 40% and preferably from 5 to 20% by weight.

The reaction mixture is passed from the reactor into the crystal separation zone which may be formed for example from a crystal separator 3 in which a vapor space 4 is formed above the liquid.

The gaseous ammonia formed in the pyrolysis passes together with vaporized solvent from the vapor space into a condensation zone which advantageously consists of a column 5 and a condenser 6. The ammonia is cooled and sucked off so that the desired pressure is set up in the system consisting of reactor and crystal separator. The solvent condensed in the column is passed back into the crystal separator. Solvent which has been condensed in condenser 9 and if necessary fresh solvent may conveniently be passed countercurrent to the vaporized solvent rising in the column into the reaction apparatus.

From the liquid reaction mixture in the crystal separator the cyanuric acid which has crystallized out and which collects at the bottom of the conical vessel is passed in the form of a thick mash containing for example from 10 to 60% and particularly from 40 to 50% by weight of solid cyanuric acid, for example by means of a pump 7 into a falling film evaporator 8 in which the cyanuric acid is freed from solvent at a temperature of from 100° to 250°C and a pressure from 1 to 300 mm. The solvent is condensed in a condenser 9 and passes thence back into the reaction zone while the dried cyanuric acid of high purity is removed from the evaporator. Space-time yields of 2 kg of cyanuric acid per liter of reaction volume per hour are achieved. Reaction volume is the total volume of reactor and crystal separator.

Liquid reaction mixture supplied in excess to the crystal separator is returned to the reaction zone. The circulation of the flowing substances through the reactor and crystal separator is effected for example by thermosyphonic circulation or by an additional conveying means provided. The temperature in the crystal separator differs from the temperature in the reactor due to the circulation.

Figure 2:
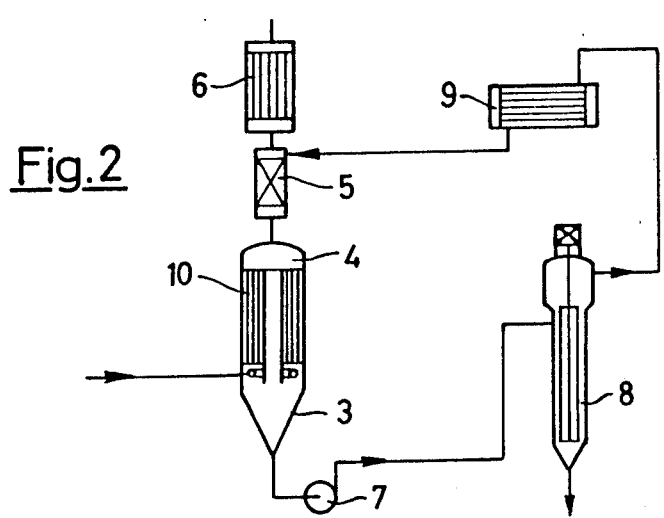

According to another embodiment of the process illustrated by FIG. 2 the pyrolysis is carried out in a circulation evaporator 10 which merges at its lower end immediately into a crystal separator 3. In this case the vapor chamber 4 is provided above the reactor constructed as a circulation evaporator.

The loss of solvent which occurs in carrying out the reaction continuously is made good by supplying fresh solvent which is introduced either into the column 5 or at some other point, for example together with the urea, in the system of reactor and crystal separator.

The loss of solvent is trivial and amounts of less than 3 g per kilogram of cyanuric acid obtained when using N-cyclohexylpyrrolidone as the solvent.

Figure 3:
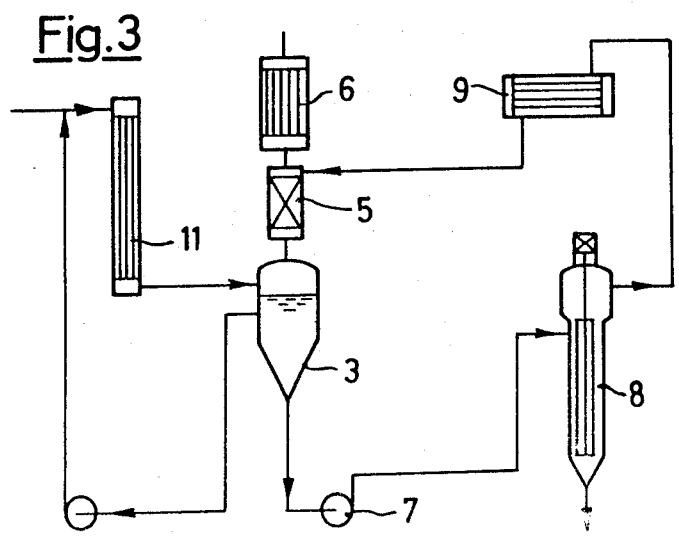

According to yet another embodiment of the invention illustrated by FIG. 3 the pyrolysis is carried out in a thin layer reactor 11 which may if desired be provided with mechanical distributing means. For example trickling film or falling film apparatus may be used as the thin layer reactors.

The new process makes possible the continuous manufacture of cyanuric acid in prolonged troublefree operation. The cyanuric acid is obtained in high purity and in yields of 99.5% of theory based on urea. Other particular advantages of the new process arise from the low consumption of solvent and energy and from the surprising fact that the cyanuric acid does not require a washing process using a more volatile solvent such as water or methanol but is obtained direct in a high purity from the reaction mixture.

The following Example illustrates the invention.

EXAMPLE

A tubular reactor 2 which is connected in the manner shown in FIG. 1 with a crystal separator 3 is charged with 2000 ml of N-cyclohexylpyrrolidone-2. The solvent flows over the tubes of the reactor. Thermosyphonic circulation is caused by heating the reactor tubes by means of the surrounding heat exchange medium; the temperature of the solvent is adjusted to 227°C. At a pressure of 300 mm 1500 parts of molten urea at 140°C is introduced per hour into the circulation through the distributor means 1. Circulation of the reaction mixture is maintained by the ammonia liberated in the pyrolysis. After a short starting-up phase 4525 parts of mash consisting of 1025 parts of cyanuric acid and 3500 parts of liquid reaction mixture is withdrawn from the crystal separator 3. This mash is passed through a pump 7 into a thin layer vertical drier 8 in which the mass is dried at 150°C and a pressure of 10 mm. The solvent thus escaping and condensed in the condenser 9 is returned continuously to the crystal separator 3 through column 5 countercurrent to the portion of solvent escaping from the crystal separator. The ammonia liberated in the pyrolysis is sucked off after cooling in the condenser 6 to about 65°C.

We claim:

1. A process for the continuous production of cyanuric acid by the pyrolysis of urea in the presence of an inert solvent wherein
   a. molten urea or a solution of urea in the solvent is fed into an externally heated tubular reactor or thin-layer reactor in which the urea is decomposed into cyanuric acid and ammonia in the presence of the solvent at a temperature of from 200° to 300°C at a pressure of from 50 to 760 mm at a space-time yield of from 0.1 to 2 kg of cyanuric acid per liter of reaction volume per hour;
   b. the reaction mixture is fed into a crystal separation zone and at the same time the mixture of ammonia and vaporous solvent is fed to a condensation zone from which the condensed solvent is returned to the reaction zone;
   c. cyanuric acid which has crystallized out from the reaction mixture in the crystal separation zone is transferred in the form of a mash to a falling film evaporator, the residual liquid reaction mixture which has been fed in excess into the crystal separation zone being returned to the reaction zone; and
   d. the mash consisting of crystallized cyanuric acid and solvent is freed from solvent in the falling film evaporator at a temperature of from 100° to 250°C and at a pressure of from 1 to 300 mm and the solvent is returned to the reaction zone after condensation.

2. A process as claimed in claim 1 wherein the liquid solvent obtained by condensation in the drying of the mash in step (d) in claim 1 is passed countercurrent to the mixture of ammonia and vaporous solvent escaping from the crystal separation zone in step (c).

3. A process as claimed in claim 1 wherein the ratio of the amounts of urea and solvent is such that the liquid reaction mixture has a solids content of from 2 to 40% by weight.

* * * * *